United States Patent [19]

Shepard et al.

[11] Patent Number: 4,544,667
[45] Date of Patent: Oct. 1, 1985

[54] 2-SULFAMOYLBENZO[B]FURAN DERIVATIVES FOR THE TREATMENT OF ELEVATED INTRAOCULAR PRESSURE

[75] Inventors: Kenneth L. Shepard, North Wales; Samuel L. Graham, Lansdale, both of Pa.

[73] Assignee: Merck & Co., Inc., Rahway, N.J.

[21] Appl. No.: 578,463

[22] Filed: Feb. 9, 1984

[51] Int. Cl.4 ............... A61K 31/34; C07D 307/82
[52] U.S. Cl. .................... 514/470; 514/229; 514/255; 514/320; 514/337; 514/397; 514/422; 514/444; 544/153; 544/376; 544/405; 546/196; 546/269; 548/336; 548/525; 549/60; 549/466
[58] Field of Search ............... 549/466, 60; 544/153, 544/405, 376; 546/196, 269; 548/336, 525; 424/248.53, 248.54, 248.55, 250, 263, 267, 273, 274, 275, 285

[56] References Cited

U.S. PATENT DOCUMENTS

| 4,386,098 | 5/1983 | Woltersdorf | 424/270 |
| 4,416,890 | 11/1983 | Woltersdorf et al. | 424/270 |
| 4,426,388 | 1/1984 | Woltersdorf | 424/270 |

FOREIGN PATENT DOCUMENTS

| 0070698 | 1/1983 | European Pat. Off. |
| 2081712 | 2/1982 | United Kingdom |

Primary Examiner—Henry R. Jiles
Assistant Examiner—Bernard I. Dentz
Attorney, Agent, or Firm—William H. Nicholson; Mario A. Monaco

[57] ABSTRACT

Novel 2-sulfamoylbenzo[b]furans and derivatives thereof are shown to be useful for the treatment of elevated intraocular pressure in compositions including opthalmic drops and inserts.

18 Claims, No Drawings

2-SULFAMOYLBENZO[B]FURAN DERIVATIVES FOR THE TREATMENT OF ELEVATED INTRAOCULAR PRESSURE

SUMMARY OF THE INVENTION

This invention relates to novel 2-sulfamoylbenzo[b]furans which are useful in the reduction of elevated intraocular pressure. More particularly this invention relates to compounds having the structural formula:

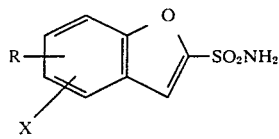

wherein R and X are as hereinafter defined, as well as the pharmaceutically and ophthalmologically acceptable salts thereof. This invention also relates to pharmaceutical compositions for systemic and ophthalmic use employing a novel compound of this invention as active ingredient for the treatment of elevated intraocular pressure, especially when accompanied by pathological damage such as in the disease known as glaucoma.

BACKGROUND OF THE INVENTION

Glaucoma is an ocular disorder associated with elevated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Indeed, few advances were made in the treatment of glaucoma since pilocarpine and physostigmine were introduced. Only recently have clinicians noted that many $\beta$-adrenergic blocking agents are effective in reducing intraocular pressure. While many of these agents are effective in reducing intraocular pressure, they also have other characteristics, e.g. membrane stabilizing activity, that are not acceptable for chronic ocular use. (S)-1-tert-Butylamino-3-[(4-morpholino-1,2,5-thiadiazol-3-yl)oxy]-2-propanol, a $\beta$-adrenergic blocking agent, was found to reduce intraocular pressure and to be devoid of many unwanted side effects associated with pilocarpine and, in addition, to possess advantages over many other $\beta$-adrenergic blocking agents, e.g. to be devoid of local anesthetic properties, to have a long duration of activity, and to display minimal tolerance.

Although pilocarpine, physostigmine and the $\beta$-blocking agents mentioned above reduce intraocular pressure, none of these drugs manifests its action by inhibiting the enzyme carbonic anhydrase and, thereby, impeding the contribution to aqueous humor formation made by the carbonic anhydrase pathway.

Agents referred to as carbonic anhydrase inhibitors, block or impede this inflow pathway by inhibiting the enzyme, carbonic anhydrase. While such carbonic anhydrase inhibitors are now used to treat intraocular pressure by oral, intravenous or other systemic routes, they thereby have the distinct disadvantage of inhibiting carbonic anhydrase throughout the entire body. Such a gross disruption of a basic enzyme system is justified only during an acute attack of alarmingly elevated intraocular pressure, or when no other agent is effective. Despite the desirability of directing the carbonic anhydrase inhibitor only to the desired ophthalmic target tissue, no topically effective carbonic anhydrase inhibitors are available for clinical use.

However, topically effective carbonic anhydrase inhibitors are reported in European Patent application Nos. 0,070,239 and 0,079,269 and U.S. application Ser. No. 364,953, now U.S. Pat. No. 4,426,388. The compounds reported therein are 5 (and 6)-hydroxy-2-benzothiazolesulfonamides and acyl esters thereof.

To be an effective and acceptable topical agent, an ophthalmic carbonic anhydrase inhibitor must not only penetrate the ophthalmic tissues to reach the active sites within the eye, but it must also be devoid of those side effects including irritation, allergic reaction and the like which would militate against long term administration.

DETAILED DESCRIPTION OF THE INVENTION

The novel compounds of this invention have the structural formula:

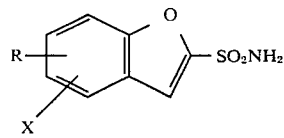

or an ophthalmologically or pharmaceutically acceptable salt thereof, wherein:
X is hydrogen, halo, such as chloro, bromo or fluoro, $C_{1-3}$alkyl, hydroxy or $C_{1-3}$alkoxy; and
R is:
(1) hydroxy,
(2) $R^1_a$ wherein $R^1_a$ is
  (a) $C_{1-18}$ alkyl either straight or branched chain and substituted with one or more of
    (i) $C_{3-6}$ cycloalkyl,
    (ii) halo, such as chloro, bromo or fluoro,
    (iii) aryl, wherein the aryl group is carbocyclic such as phenyl or napthyl, or heterocyclic such as pyridinyl, furanyl, pyrazinyl, morpholinyl, oxazolinyl, dioxolinonyl, imidazolyl, thienyl or the like and wherein the aryl group can be substituted with one or more of $C_{1-10}$ alkyl, halo, $C_{1-4}$ alkoxy or $C_{2-5}$ alkanoyl,
    (iv) hydroxy,
    (v) $C_{1-3}$ alkoxy,
    (vi) aryl-$C_{1-3}$ alkoxy,
    (vii) amino,
    (viii) ($C_{1-3}$ alkyl)amino,
    (ix) di ($C_{1-3}$ alkyl)amino,
    (x)

wherein $R^2$ is
    (1) HO-,
    (2) $M^+O^-$, wherein $M^+$ is a pharmaceutically acceptable cation such as that from an alkali metal, or an ammonium,
    (3) $C_{1-10}$ alkoxy, (4) R³R⁴N- wherein R³ and R⁴ are independently hydrogen, C₁₋₁₅ alkyl, or taken together form a 3-7 membered heterocycle with the nitrogen to which they are attached such as piperidino or pyrrolidino;
(b) C₃₋₆ cycloalkyl,
(c) C₁₋₁₈ alkyl-C₃₋₆ cycloalkyl,
(d) aryl as previously defined,
(e) C₂₋₆ alkenyl,
(f) aryl-C₂₋₆ alkenyl,
(g) C₂₋₆ alkynyl,
(3) R¹ₐ-O-,
(4)

wherein R¹ is R¹ₐ or C₁₋₁₈ alkyl,
(5)

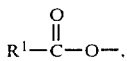

(6)

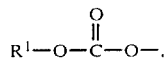

(7)

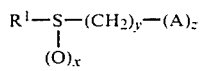

wherein x is 0–2; y is 0–3; z is 0 or 1; and A is a heteroatom such as S, O, or N,
(8)

where
R⁵ and R⁶ are independently:
(a) hydrogen,
(b) C₁₋₁₈ alkyl, either straight or branched chain,
(c) C₃₋₆ cycloalkyl,
(d) C₃₋₆ cycloalkyl-C₁₋₃ alkyl,
(e) aryl-C₁₋₃ alkyl wherein the aryl group is either unsubstituted or substituted with one or more of chloro, bromo, fluoro, C₁₋₃ alkyl or C₁₋₃ alkoxy,
(f)

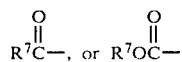

wherein R⁷ is
(i) C₁₋₁₈ alkyl, either straight or branched chain,
(ii) aryl, either unsubstituted or substituted with one or more of chloro, bromo, fluoro, C₁₋₃ alkyl, or C₁₋₃ alkoxy,
(iii) aryl-C₁₋₃ alkyl wherein the aryl group is either unsubstituted or substituted with one or more of chloro, bromo, fluoro, C₁₋₃ alkyl or C₁₋₃ alkoxy, (iv) amino-C₁₋₁₈ alkyl either straight or branched chain; or
(g) R⁵ and R⁶ if lower alkyl, are joined together directly or through a heteroatom selected from O or N to form a 5 or 6 membered heterocycle with the nitrogen to which they are attached such as pyrrolidine, piperidine, morpholine, or piperazine.
(9)

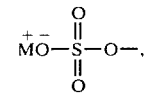

wherein M⁺ is an ophthalmologically acceptable cation selected from sodium, potassium ammonium, tetra(C₁₋₄alkyl)ammonium, pyridinium, imidazolium, pralidoxime, and thiamine
(10)

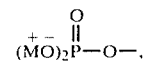

wherein M⁺ is as previously defined;
(11)

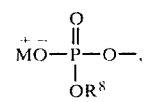

wherein R⁸ is C₁₋₃ alkyl or phenyl -C₁₋₃ alkyl; or
(12)

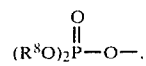

wherein R⁸ is as previously defined, and the two may be the same or different.

In the preferred embodiments of this invention, X is hydrogen and R is HO-,

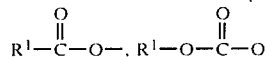

or R⁵R⁶N-, especially wherein R¹ is C₁₋₁₈alkyl, and more especially C₁₋₄alkyl. It is also preferred that the substituent R be in the 5- or 6-position of the benzo[b]furan.

Preferred species of this invention are:
5(or 6)-hydroxy-2-sulfamoylbenzo[b]furan;
5(or 6)-(2-sulfamoylbenzo[b]furyl) acetate;
5(or 6)-(2-sulfamoylbenzo[b]furyl) 2,2-dimethylpropionate;
5(or 6)-(2-sulfamoylbenzo[b]furyl) 2-methylpropionate;
5(or 6)-(2-sulfamoylbenzo[b]furyl) 3-ethoxycarbonylpropionate.

Representative carbonic anhydrase inhibitors of this invention include:
5(or 6)-hydroxy-2-sulfamoylbenzo[b]furan;
5(or 6)-(2-sulfamoylbenzo[b]furyl) benzoate;
5(or 6)-(2-sulfamoylbenzo[b]furyl) propionate;
5(or 6)-(2-sulfamoylbenzo[b]furyl) butyrate;

5(or 6)-(2-sulfamoylbenzo[b]furyl) 2,2-dimethylpropionate;
5(or 6)-(2-sulfamoylbenzo[b]furyl) octanoate;
5(or 6)-(2-sulfamoylbenzo[b]furyl) dodecanoate;
5(or 6)-(2-sulfamoylbenzo[b]furyl) 4,4-dimethylcyclohexane carboxylate;
5(or 6)-(2-sulfamoylbenzo[b]furyl) 3-chloro-2,2-dimethylpropionate;
5(or 6)-(2-sulfamoylbenzo[b]furyl) 4-methylbenzoate;
5(or 6)-(2-sulfamoylbenzo[b]furyl) 4-chlorobenzoate;
5(or 6)-(2-sulfamoylbenzo[b]furyl) 4-methoxybenzoate;
5(or 6)-(2-sulfamoylbenzo[b]furyl) 2-(4-chlorophenyl)acetate;
5(or 6)-(2-sulfamoylbenzo[b]furyl) 3-(4-ethylphenyl)propionate;
5(or 6)-(2-sulfamoylbenzo[b]furyl) 3-hydroxy-2,2-dimethylpropionate;
5(or 6)-(2-sulfamoylbenzo[b]furyl) 4-aminobutyrate HCl;
5(or 6)-(2-sulfamoylbenzo[b]furyl) acrylate;
5(or 6)-(2-sulfamoylbenzo[b]furyl) crotonate;
5(or 6)-(2-sulfamoylbenzo[b]furyl) propiolate;
5(or 6)-(2-sulfamoylbenzo[b]furyl) 3-phenyl-2-propenoate;
5(or 6)-(2-sulfamoylbenzo[b]furyl) cyclopentaneacetate;
5(or 6)-(2-sulfamoylbenzo[b]furyl) phenylacetate;
5(or 6)-(2-sulfamoylbenzo[b]furyl) cyclohexanecarboxylate;
5(or 6)-(2-sulfamoylbenzo[b]furyl) acetate;
5(or 6)-(2-sulfamoylbenzo[b]furyl) 3-carboxypropionate;
5(or 6)-(2-sulfamoylbenzo[b]furyl) 3-carboxypropionate, sodium salt;
5(or 6)-(2-sulfamoylbenzo[b]furyl) 2-ethoxycarbonylacetate;
5(or 6)-(2-sulfamoylbenzo[b]furyl) acetoacetate;
5(or 6)-(2-sulfamoylbenzo[b]furyl) 3-aminocarbonylpropionate;
5(or 6)-(2-sulfamoylbenzo[b]furyl) N-acetylpiperidine-4-carboxylate;
5(or 6)-(2-sulfamoylbenzo[b]furyl) nicotinoate;
5(or 6)-(2-sulfamoylbenzo[b]furyl) 1-methyl-4-imidazolylacetate;
5(or 6)-(2-sulfamoylbenzo[b]furyl) 2-methoxybutyrate;
5(or 6)-(2-sulfamoylbenzo[b]furyl) 2-methoxysuccinate;
5(or 6)-(2-sulfamoylbenzo[b]furyl) phenyl carbonate;
5(or 6)-(2-sulfamoylbenzo[b]furyl) ethyl carbonate;
5(or 6)-(2-sulfamoylbenzo[b]furyl) propyl carbonate;
5(or 6)-(2-sulfamoylbenzo[b]furyl) 1,1-dimethylethyl carbonate;
5(or 6)-(2-sulfamoylbenzo[b]furyl) n-heptyl carbonate;
5(or 6)-(2-sulfamoylbenzo[b]furyl) undecanyl carbonate;
5(or 6)-(2-sulfamoylbenzo[b]furyl) 4,4-dimethylcyclohexyl carbonate;
5(or 6)-(2-sulfamoylbenzo[b]furyl) 2-chloro-1,1-dimethylethyl carbonate;
5(or 6)-(2-sulfamoylbenzo[b]furyl) 4-methylphenyl carbonate;
5(or 6)-(2-sulfamoylbenzo[b]furyl) 4-chlorophenyl carbonate;
5(or 6)-(2-sulfamoylbenzo[b]furyl) 4-methoxyphenyl carbonate;
5(or 6)-(2-sulfamoylbenzo[b]furyl) -4-chlorobenzyl carbonate;
5(or 6)-(2-sulfamoylbenzo[b]furyl) 2-(4-ethylphenyl)ethyl carbonate;
5(or 6)-(2-sulfamoylbenzo[b]furyl) 2-methylpropyl carbonate;
5(or 6)-(2-sulfamoylbenzo[b]furyl) allyl carbonate;
5(or 6)-(2-sulfamoylbenzo[b]furyl) 2-propynyl carbonate;
5(or 6)-(2-sulfamoylbenzo[b]furyl) 3-phenyl-2-propenyl carbonate;
5(or 6)-(2-sulfamoylbenzo[b]furyl) cyclopentylmethyl carbonate;
5(or 6)-(2-sulfamoylbenzo[b]furyl) benzyl carbonate;
5(or 6)-(2-sulfamoylbenzo[b]furyl) cyclohexyl carbonate;
5(or 6)-(2-sulfamoylbenzo[b]furyl) methyl carbonate;
5(or 6)-amino-2-sulfamoylbenzo[b]furan;
5(or 6)-ethylamino-2-sulfamoylbenzo[b]furan;
5(or 6)-diethylamino-2-sulfamoylbenzo[b]furan;
5(or 6)-[(1-methylethyl)amino]-2-sulfamoylbenzo[b]furan;
5(or 6)-[N-ethyl-N-(2-propyl)amino]-2-sulfamoylbenzo[b]furan;
5(or 6)-[(N-benzyl-N-ethyl)amino]-2-sulfamoylbenzo[b]furan;
5(or 6)-cyclohexylamino-2-sulfamoylbenzo[b]furan;
5(or 6)-cyclopentylmethylamino-2-sulfamoylbenzo[b]furan;
5(or 6)-pivaloylamino-2-sulfamoylbenzo[b]furan;
5(or 6)-[(N-methyl-N-pivaloyl)amino]-2-sulfamoylbenzo[b]furan;
5(or 6)-pivaloyloxycarbonylamino-2-sulfamoylbenzo[b]furan;
5(or 6)-acetylamino-2-sulfamoylbenzo[b]furan;
5(or 6)-butyrylamino-2-sulfamoylbenzo[b]furan;
5(or 6)-benzoylamino-2-sulfamoylbenzo[b]furan;
5(or 6)-[(4-methylbenzoyl)amino]-2-sulfamoylbenzo[b]furan;
5(or 6)-[(4-fluorobenzoyl)amino]-2-sulfamoylbenzo[b]furan;
5(or 6)-(4-methoxybenzoyl)amino-2-sulfamoylbenzo[b]furan;
5(or 6)-nicotinoylamino-2-sulfamoylbenzo[b]furan;
5(or 6)-thienylcarbonylamino-2-sulfamoylbenzo[b]furan;
5(or 6)-alanylamino)-2-sulfamoylbenzo[b]furan;
5(or 6)-(N-ethyl-N-hydroxy)amino-2-sulfamoylbenzo[b]furan;
5(or 6)-(N-ethyl-N-methoxy)amino-2-sulfamoylbenzo[b]furan;
5(or 6)-(1-morpholino)-2-sulfamoylbenzo[b]furan;
2-sulfamoylbenzo[b]furan-6(or 5)-acetic acid;
2-sulfamoylbenzo[b]furan-6(or 5)-propionic acid;
5(or 6)-(2-hydroxyethyl)-2-sulfamoylbenzo[b]furan;
5(or 6)-(2,3-dihydroxypropoxy)-2-sulfamoylbenzo[b]furan;
5(or 6)-(dioxolin-2-one-4-ylmethoxy)-2-sulfamoylbenzo[b]furan;
5(or 6)-(5-oxazolinylmethoxy)-2-sulfamoylbenzo[b]furan;
5(or 6)-(1-methylimidazol-4-yloxy)-2-sulfamoylbenzo[b]furan;
5(or 6)-furfuryl-2-sulfamoylbenzo[b]furan;
5(or 6)-(2-morpholinylethyl)-2-sulfamoylbenzo[b]furan;
5(or 6)-morpholinylmethyl-2-sulfamoylbenzo[b]furan;

5(or 6)-hydroxymethyl-2-sulfamoylbenzo[b]furan;
5(or 6)-(acetyloxymethyl-2-sulfamoylbenzo[b]furan;
5(or 6)-(2-acetyloxyethyl)-2-sulfamoylbenzo[b]furan;
5(or 6)-benzoyl-2-sulfamoylbenzo[b]furan;
5(or 6)-propionyl-2-sulfamoylbenzo[b]furan;
5(or 6)-butyryl-2-sulfamoylbenzo[b]furan;
5(or 6)-(2,2-dimethylpropionyl)-2-sulfamoylbenzo[b]furan;
5(or 6)-octanoyl-2-sulfamoylbenzo[b]furan;
5(or 6)-dodecanoyl-2-sulfamoylbenzo[b]furan;
5(or 6)-(4,4-dimethylcyclohexanecarbonyl)-2-sulfamoylbenzo[b]furan;
5(or 6)-(3-chloro-2,2-dimethylpropionyl)-2-sulfamoylbenzo[b]furan;
5(or 6)-(2-methylbenzoyl)-2-sulfamoylbenzo[b]furan;
5(or 6)-(4-chlorobenzoyl)-2-sulfamoylbenzo[b]furan;
5(or 6)-(4-methoxybenzoyl)-2-sulfamoylbenzo[b]furan;
5(or 6)-(4-chlorophenylacetyl)-2-sulfamoylbenzo[b]furan;
5(or 6)-[3-(4-ethylphenyl)propionyl)]-2-sulfamoylbenzo[b]furan;
5,6-dihydroxy-2-sulfamoylbenzo[b]furan;
5,6-dimethoxy-2-sulfamoylbenzo[b]furan;
5-hydroxy-6-methoxy-2-sulfamoylbenzo[b]furan;
6-hydroxy-5-methoxy-2-sulfamoylbenzo[b]furan; and
5,6-methylenedioxy-2-sulfamoylbenzo[b]furan.
5(or 6)-(3-hydroxy-2,2-dimethylpropionyl)-2-sulfamoylbenzo[b]furan;
5(or 6)-(4-aminobutyryl)-2-sulfamoylbenzo[b]furan;
5(or 6)-(acryloyl)-2-sulfamoylbenzo[b]furan;
5(or 6)-(crotonyl)-2-sulfamoylbenzo[b]furan;
5(or 6)-propiolyl-2-sulfamoylbenzo[b]furan;
5(or 6)-(3-phenyl-2-propenoyl)-2-sulfamoylbenzo[b]furan;
5(or 6)-cyclopentaneacetyl-2-sulfamoylbenzo[b]furan;
5(or 6)-phenylacetyl-2-sulfamoylbenzo[b]furan;
5(or 6)-cyclohexanecarbonyl-2-sulfamoylbenzo[b]furan;
5(or 6)-acetyl-2-sulfamoylbenzo[b]furan;
5(or 6)-(3-carboxypropionyl)-2-sulfamoylbenzo[b]furan;
5(or 6)-ethoxycarbonylacetyl-2-sulfamoylbenzo[b]furan;
5(or 6)-acetoacetyl-2-sulfamoylbenzo[b]furan;
5(or 6)-(3-aminocarbonylpropionyl)-2-sulfamoylbenzo[b]furan;
5(or 6)-(N-acetylpiperidine-4-carbonyl)-2-sulfamoylbenzo[b]furan;
5(or 6)-(4-imidazolyl)-2-sulfamoylbenzo[b]furan;
5(or 6)-pyrazinyl-2-sulfamoylbenzo[b]furan;
5(or 6)-(4-imidazolylcarbonyl)-2-sulfamoylbenzo[b]furan;
5(or 6)-(4-imidazolylsulfonyl)-2-sulfamoylbenzo[b]furan;
5(or 6)-(trifluoromethylsulfonyl)-2-sulfamoylbenzo[b]furan.

The key intermediate methoxy-2-sulfamoylbenzo[b]furans are prepared by treating the corresponding methoxybenzo[b]furan with at least a molar equivalent of n-butyl lithium in an inert solvent such as tetrahydrofuran at a reduced temperature, preferably below −10° C., most suitably at −70° C. Sulfur dioxide gas is then passed over the solution at a rate such that the reaction mixture does not exceed a temperature of −10° C. After the reaction is complete, the solvents are removed and the product reacted with at least a molar equivalent of N-chlorosuccinimide at reduced temperature, generally 0° C. or less. The mixture is then treated with concentrated aqueous ammonia and the resulting methoxy-2-sulfamoylbenzo[b]furan is collected and purified by crystallization.

The novel process for preparing the compounds wherein R is hydroxy comprises treatment of a methoxy-2-sulfamoylbenzo[b]furan with at least an equimolar amount of pyridine hydrochloride at a temperature from about the fusion point to about 200° C., and preferably from about 180°–190° C. for from about 1 to 4 hours, preferably about 2 hours, until the reaction is substantially complete.

The novel process to prepare those compounds wherein R is

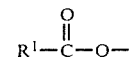

is represented by the following reaction scheme:

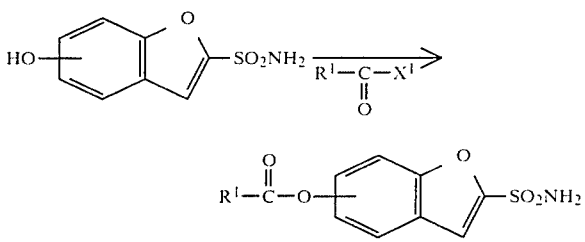

where $R^1$ has the meanings hereinbefore designated, and $X^1$ is chloro, bromo, iodo,

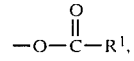

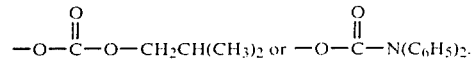

Generally equimolar amounts of the hydroxy-2-sulfamoylbenzo[b]furan and

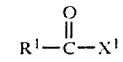

are employed, although use of an excess of the more readily available reactant is satisfactory.

The reaction is conducted in a suitable, inert solvent such as acetone, dimethylformamide, pyridine, ethyl acetate, tetrahydrofuran or benzene and the like with at least an equimolar amount of a hydrohalide acceptor when the acylating agent is an acyl halide or with a carboxylic acid acceptor when the acylating agent is an acid anhydride. Bases such as triethylamine, pyridine and the like may be employed for this purpose.

The reaction may be conducted with or without a catalyst at temperatures of from 0° C. to the boiling point of the solvent used but preferably from about 15° C. to 50° C.

When a catalyst is employed, a 4,4-dialkylaminopyridine such as 4-dimethylaminopyridine or 4-pyrrolidinopyridine is preferred.

The compounds wherein R is

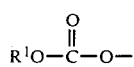

of this invention are most suitably prepared by reacting a compound

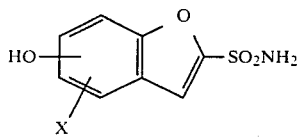

with an appropriate haloformate, particularly a chloroformate of the formula:

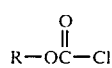

or a bis carbonate of the formula:

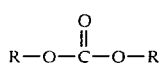

The reaction is conducted in a suitable solvent such as dimethylformamide, pyridine, acetone, ethyl acetate, tetrahydrofuran or benzene and the like with at least an equimolar amount of a hydrohalide acceptor. Bases such as triethylamine, pyridine and the like may be employed for this purpose.

The reaction may be conducted with or without a catalyst at temperatures of from 0° C. to the boiling point of the solvent used but preferably from 15° C. to 50° C.

When a catalyst is employed, triethylamine or a 4,4-dialkylaminopyridine such as 4-dimethylaminopyridine or 4-pyrrolidinopyridine is preferred.

In the novel process of this invention for preparing the ethers of hydroxy-2-sulfamoylbenzo[b]furans, the hydroxy compound is treated with an "alkylating" agent of formula $R^1$-$X^2$ wherein $X^2$ is a halide such as chloride, bromide or iodide, or other good leaving group such as mesylate, tosylate or benzenesulfonate in a suitable solvent such as dimethyl formamide, hexamethyl phosphoramide, or the like in the presence of a base such as an alkali metal alkoxide, preferably sodium methoxide, at about 0° C. to 35° C., usually about room temperature for about 10 to 30 hours.

An alternate synthesis of ethers comprises protecting the sulfonamide group as an N,N-disubstituted formamidine which is removed after formation of the desired ether. The formamidine derivative is prepared by adding, for example, N,N-dimethylformamide dimethylacetal to a suspension of the hydroxy-2-sulfamoylbenzo[b]furan in an inert organic solvent such as acetonitrile at about −10° to +35° C., preferably room temperature for about 0.5 to about 3 hours.

The ethers are then readily prepared by treating the hydroxy compound with the "alkylating" agent, $R^1$-$X^2$, in a solvent such as dimethyl sulfoxide, preferably in the presence of an acid acceptor such as potassium carbonate or the like, pyridine or the like or basic ion exchange resin. The reaction is conducted at about 25° to 100° C., preferably about 60° C., for about 10 to 36 hours, preferably about 18 hours.

The protecting group is then removed from the sulfonamide by treating the compound with dilute alkali such as 2 N sodium hydroxide at about 20° to 60° C., preferably about 40° C. for about 0.5 to 3 hours, preferably about 1 hour. Also, 6N HCl at about 100° C. for 2–5 hours can be used to effect the desired deprotection.

The novel compounds of this invention with no substituent, i.e. R═H and those carrying fairly stable substituents such as wherein R is $R^1$ and $R^1$ is alkyl, cycloalkyl, cycloalkyl-alkyl, alkylcycloalkyl, alkoxyalkyl, alkenyl; R is $R^1$-O-wherein $R^1$ is as defined above; R is $R^5R^6$-N-wherein $R^5$ and $R^6$ are not hydrogen are conveniently prepared by formation of the sulfonamide group on the intact benzo[b]furan moiety. This is accomplished by the procedure described earlier for preparation of methoxy-2-sulfamoylbenzo[b]furans.

The O-sulfates of this invention are prepared by reacting an hydroxy-2-sulfamoylbenzo[b]-furan with sulfamic acid in pyridine at elevated temperatures (about 50° to the boiling point) for about 18 to 48 hours to provide the ammonium salt followed, if desired, by titration with hydroxides of the formula MOH to provide the other salts.

Similarly the O-phosphates of this invention are prepared by treatment of a hydroxy-2-sulfamoylbenzo[b]furan with phosphorus oxychloride, an alkyl dichlorophosphate or a dialkyl chlorophosphate in pyridine or similar basic solvent at about −5° to +5° C. for about 0.25 to 1.0 hour.

EXAMPLE 1

5-Hydroxy-2-sulfamoylbenzo[b]furan

Step A: Preparation of 5-Methoxy-2-sulfamoylbenzo[b]furan

A solution of 5-methoxybenzo[b]furan (10.8 g, 73 mmol) in 100 ml of dry THF was cooled to −65° C. A 1.6M solution of n-butyllithium in hexane (50 ml, 80 mmol) was added rapidly, dropwise, such that the temperature did not exceed −55° C. After 15 minutes at −55° C. sulfur dioxide gas was passed into the reaction flask until an aliquot removed from the flask and dissolved in water was no longer basic to pH paper. Hexane (100 ml) was added to precipitate the product. After warming to room temperature, the product was isolated by filtration. The crude product was dried under low vacuum for 18 hours at room temperature, yielding 15.6 g (98%) of a tan powder.

The dry sulfinate salt so obtained was suspended in 150 ml $CH_2Cl_2$ and cooled to 5° C. prior to adding 10.7 g of N-chlorosuccinimide (80 mmol). Stirring was continued for 15 minutes at 5° C. and the cooling bath was removed. After an additional 15 minutes the suspension was filtered through a pad of filter aid. Evaporation of the solvent furnished 17.2 g of sulfonyl chloride as a brown solid. This material was dissolved in 50 ml of dry acetone and added over a 1 minute period to a chilled (5° C.) stirring solution of 15 ml $NH_4OH$ in 150 ml acetone. After 30 minutes the solvent was evaporated. The residue was partitioned between water and ethyl acetate. The organic phase was washed with brine and dried ($Na_2SO_4$). Evaporation left 17.2 g of brown solid. The pure compound was obtained by recrystallization from dichloroethane; m.p. 119°–120° C.

Analysis calculated for $C_9H_9NO_4S$: C, 47.57; N, 6.16; H, 3.99; Found: C, 47.52; N, 6.14; H, 4.02.

'H NMR (d₆-acetone) 7:7.50 (1H, d, J=9), 7.30 (1H, s), 7.25 (1H, d, J=3), 7.1 (1H, dd, J=9, 3), 3.83 (3H, s).

Step B: Preparation of
5-Hydroxy-2-sulfamoylbenzo[b]furan

A 6.2 g sample of 5-methoxy-2-sulfamoylbenzo[b]furan was heated with 30 g of pyridine hydrochloride at 198°–200° C. for 15 minutes. The hot solution was poured onto ice water (300 ml) and the product was extracted into ethyl acetate. The organic extract was washed with 1N HCl, saturated NaHCO₃ and brine. After drying (Na₂SO₄) the solvent was evaporated yielding 4.4 g of tan solid. This crude product was dissolved in boiling water and treated with decolorizing carbon. The hot solution was filtered. Upon cooling brown needles separated which were isolated by filtration. After drying in vacuo (70° C., house vacuum) the product weighed 2.9 g, m.p. 166°–168° C.

Analysis calculated for $C_8H_7NO_4S$: C, 45.07; N, 6.57; H, 3.31; Found: C, 45.19; N, 6.54; H, 3.29.

'H NMR (DMSO-d₆)δ: 9.48 (1H, s), 7.91 (2H, s), 7.50 (1H, d, J=9), 7.30 (1H, s), 7.08 (1H, d, J=2.5), 6.95 (1H, dd, J=9, 2.5)

EXAMPLE 2

Employing the procedure substantially as described in Example 1, but substituting for the 5-methoxybenzo[b]furan used therein, an equimolar amount of 6-methoxybenzo[b]furan there was obtained 6-hydroxy-2-sulfamoylbenzo[b]furan (m.p. 185°–187° C.) via the intermediate 6-methoxy-2-sulfamoylbenzo[b]furan (m.p. 148°–149° C.)

EXAMPLE 3

4-Hydroxy-2-sulfamoylbenzo[b]furan

Employing the procedure substantially as described in Example 1, but starting with 4-methoxybenzo[b]furan, there are produced, in sequence in approximately the same yield, 4-methoxy-2-sulfamoylbenzo[b]furan and 4-hydroxy-2-sulfamoylbenzo[b]furan.

EXAMPLE 4

7-Hydroxy-2-sulfamoylbenzo[b]furan

Employing the procedure substantially as described in Example 1, but starting with 7-methoxybenzo[b]furan, there are produced in sequence 7-methoxy-2-sulfamoylbenzo[b]furan; and 7-hydroxy-2-sulfamoylbenzo[b]furan.

EXAMPLE 5

6-(2-Sulfamoylbenzo[b]furyl) Acetate

A solution of 6-hydroxy-2-sulfamoylbenzo[b]furan (2.32 g, 0.0109 mole) in acetone (45 ml) at −5° is treated with triethylamine (1.2133 g; 0.01199 mole). A solution of acetyl chloride (0.9413 g, 0.01199 mole) in acetone (5 ml) is added to the reaction mixture, dropwise, during 15 minutes at −5° C. After 15 minutes, the reaction mixture is filtered to remove the precipitated triethylamine hydrochloride. The filtrate is evaporated in vacuo. The residue is dissolved in ethyl acetate, washed with a small quantity of water and saturated sodium chloride solution, dried over sodium sulfate and concentrated to dryness in vacuo to give the product, m.p. 138°–139° C.

Similarly prepared are the 4,5- and 7-(2-sulfamoylbenzo[b]furyl) acetates.

Employing the procedure described in Example 5, but using as starting materials either the 4-, 5-, 6-, or 7-hydroxy-2-sulfamoylbenzo[b]furan and the acid chlorides described in Table I, there are produced the acyloxy-2-sulfamoylbenzo[b]furans also described in Table I in accordance with the following reaction scheme:

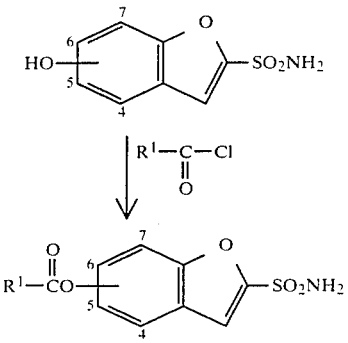

TABLE I

| Position of Substitution | $-R^1-\overset{\overset{O}{\|}}{C}-O-$ |
|---|---|
| 6 | propionate |
| 4 | cyclohexanecarboxylate |
| 7 | cyclopentanecarboxylate |
| 5 | octanoate |
| 5 | 4,4-dimethylcyclohexanecarboxylate |
| 6 | 3-chloro-2,2-dimethylpropionate |
| 5 | acetate (m.p. 178–181° C.) |
| 6 | 2,2-dimethylpropionate (m.p. 122–124° C.) |
| 5 | 2,2-dimethylpropionate (m.p. 130–131° C.) |
| 5 | benzoate |
| 6 | nicotinate |
| 4 | 4-methylbenzoate |
| 5 | 4-chlorobenzoate |
| 7 | 4-methoxybenzoate |
| 5 | 3-phenylpropionate |
| 6 | 4-chlorophenylacetate |
| 5 | 3-(4-ethylphenyl)propionate |
| 5 | 3-hydroxy-2,2-dimethylpropionate |
| 5 | 3-dimethylamino-2,2-dimethylpropionate |
| 6 | acrylate |
| 7 | crotonate |
| 4 | propiolate |
| 5 | cinnamate |
| 5 | 3-methoxycarbonylpropionate |
| 6 | 3-ethoxycarbonylpropionate |
| 5 | N—acetylpiperidine-4-carboxylate |
| 6 | methoxyacetate |
| 5 | succinate[1] |
| 5 | 2-methoxy-2-methylpropionate[2] |
| 5 | 2-thienylcarboxylate |

[1]acylating reagent is succinic anhydride
[2]acylating reagent is 2-methoxy-2-methylpropionic N,N—diphenyl carbamic anhydride

EXAMPLE 6

6-(2-Sulfamoylbenzo[b]furyl) 2-Methylpropyl Carbonate

A solution of 6-hydroxy-2-sulfamoylbenzo[b]furan (0.01 mole) in acetone (45 ml) at −5° is treated with triethylamine (1.21 g; 0.01 mole). Then a solution of isobutyl chloroformate (1.64 g; 0.012 mole) in acetone (5 ml) is added, dropwise, during 15 min. at −5° C.

After 15 minutes, the reaction mixture is poured into water (300 ml). The resulting semi-solid is extracted into ethyl acetate, washed with saturated sodium chloride solution and dried over sodium sulfate. Removal of solvent in vacuo gives the product which is recrystalized from butyl chloride.

Employing the procedure substantially as described in Example 6 but substituting for the 6-hydroxy-2-sulfamoylbenzo[b]furan used therein equimolecular amounts of the 4,5 or 7-hydroxy-2-sulfamoylbenzo[b]furans and using isobutyl chloroformate as in Example 6 or substituting therefore the chloroformates described in Table II, there are produced the 4-,5-,6- or 7-(2-sulfamoylbenzo[b]furyl) carbonates also described in Table II in accordance with the following reaction scheme:

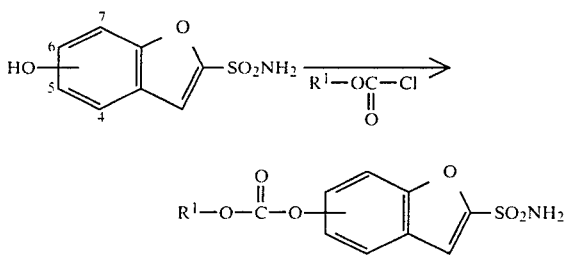

TABLE II

| Position of Substitution | R¹ |
| --- | --- |
| 5 | 2-methylpropyl |
| 5 | 2-methylpropyl |
| 7 | 2-methylpropyl |
| 6 | phenyl |
| 6 | ethyl |
| 6 | propyl |
| 6 | 1,1-dimethylethyl |
| 5 | n-heptyl |
| 5 | undecanyl |
| 4 | 4,4-dimethylcyclohexyl |
| 7 | 2-chloro-1,1-dimethylethyl |
| 6 | 4-methylphenyl |
| 5 | 4-chlorophenyl |
| 4 | 4-methoxyphenyl |
| 7 | 4-chlorobenzyl |

EXAMPLE 7

(S)-6-[3-(1,1-Dimethylethyl)oxazolidin-2-on-5-yl]methoxy-2-sulfamoylbenzo[b]furan Step A: Preparation of N,N-Dimethyl-N'-(6-hydroxy-2-sulfamoylbenzo[b]furan)formamidine The title compound is prepared by treating 6-hydroxy-2-sulfamoylbenzo[b]furan with a slight excess of N,N-dimethylformamide dimethyl acetal.

Step B: Preparation of (S)-N,N-Dimethyl-N'-[[3-(1,1-dimethylethyl)oxazolidin-2-on-5-yl]methoxy-2-sulfamoylbenzo[b]furan]formamidine The title compound is prepared by alkylation of the product from Step A with (S)-3-(1,1-dimethylethyl)-5-(hydroxymethyl)oxazolidinone mesylate.

Step C: Preparation of (S)-6-[3-(1,1-Dimethylethyl)oxazolidin-2-on-5-yl]methoxy-2-sulfamoylbenzo[b]furan This compound is prepared by hydrolysis with hot hydrochloric acid of the product from Step B.

Similarly prepared are the (S)-4-,5- or 7-[3-(1,1-dimethylethyl)oxazolidin-2-on-5-yl]methoxy-2-sulfamoylbenzo[b]furans, respectively.

EXAMPLE 8

(S)-6-[(Oxazolidin-2-on-5-yl)methoxy]-2-sulfamoylbenzo[b]furan

Crude by-product isolated from Step C of Example 7 is dissolved in hot ethyl acetate/acetonitrile, treated with charcoal, and the solvents are boiled off until crystallization begins. The product is collected by filtration and dried.

Similarly prepared are the (S)-4-,5- or 7-[(oxazolidin-2-on-5-yl)methoxy]-2-sulfamoylbenzo[b]furans.

EXAMPLE 9

(S)-6-[3-(1,1-Dimethylethylamino)-2-hydroxypropoxy-2-sulfamoylbenzo[b]furan Hydrochloride The title compound is prepared by alkaline hydrolysis (40% NaOH) of the product from Example 7, Step C.

Similarly prepared are the (S)-4-,5- or 7-[3-(1,1-dimethylethylamino)-2-hydroxypropoxy]-2-sulfamoylbenzo[b]furan.

EXAMPLE 10

6-(2-Ketopropoxy)-2-sulfamoylbenzo[b]furan

Step A: Preparation of N,N-Dimethyl-N'-[6-(2-ketopropoxy)-2-sulfamoylbenzo[b]furan formamidine Chloroacetone (1.2 ml) is added dropwise to a stirred mixture of anhydrous potassium carbonate (2.0 g) and N,N-dimethyl-N'-[6-hydroxy-2-sulfamoyl-benzo[b]furan]formamidine (2.60 g) in dimethylsulfoxide (20 ml) at 25° C. After 24 hours, the reaction mixture is diluted with water (200 ml) and the solid that forms is collected and dried.

Step B: Preparation of 6-(2-Ketopropoxy)-2-sulfamoylbenzo[b]furan

The product from Step A is heated to reflux with a mixture of methanol (50 ml) and 6N hydrochloric acid (50 ml) for 0.5 hour. The cooled solution is diluted with water (300 ml) and chilled. The precipitated solid is collected, washed with water, dried and recrystallized from acetonitrile.

Similarly prepared are the 4-,5- or 7-(2-ketopropoxy)-2-sulfamoylbenzo[b]thiophenes.

EXAMPLE 11

6-[(Ethoxycarbonyl)methoxy]-2-sulfamoylbenzo[b]furan

The title compound is produced by alkylation of 6-hydroxy-2-sulfamoylbenzo[b]furan with ethyl bromoacetate.

Similarly produced are the 4-,5- or 7-[(ethoxycarbonyl)methoxy]-2-sulfamoylbenzo[b]furan.

EXAMPLE 12

6-[(Carboxy)methoxy]-2-sulfamoylbenzo[b]furan

Solid 6-[(ethoxycarbonyl)methoxy]-2-sulfamoylbenzo[b]furan (5 mmol) is added to 10% NaOH (40 ml) and stirred at room temperature 4-6 hours. The solution is acidified and extracted with ethyl acetate, dried (Na$_2$SO$_4$) and evaporated. The residue is dissolved in hot ethyl acetate, filtered, and evaporated until crystallization begins to give product.

By similar procedures there are prepared the 4-,5- or 7-[(carboxy)methoxy]-2-sulfamoylbenzo[b]furan.

EXAMPLE 13

6-[3-Carboxypropoxy]-2-sulfamoylbenzo[b]furan

Step A: Preparation of N,N-Dimethyl-N'-[6-(3-(ethoxycarbonyl)propoxy)-2-sulfamoylbenzo[b]furan formamidine Ethyl-4-bromobutyrate (2.15 g, 11.0 mmol) is added dropwise to a stirred solution of N,N-dimethyl-N'-[6-hydroxy-2-sulfamoylbenzo[b]furan formamidine (10.0 mmol) and potassium carbonate (2.07 g, 15.0 mmol) in dimethyl sulfoxide (20.0 ml). The reaction temperature is kept at 70° C. for 18 hours. The reaction mixture is cooled, poured into water (100 ml) and extracted with ethyl acetate (3×150 ml). The combined ethyl acetate extracts are washed with water (3×50 ml), brine (2×25 ml) and dried (Na$_2$SO$_4$). The ethyl acetate is removed under vacuum to yield the product.

Step B: Preparation of 6-(3-carboxypropoxy)-2-sulfamoylbenzo[b]furan

N,N-Dimethyl-N'-[6-(3-(ethoxycarbonyl)propoxy)-2-sulfamoylbenzo[b]furan]formamidine (7.2 mmol) is suspended in hydrochloric acid (25.0 ml, 6.0N) and warmed to 70° C. for 6 hours. The reaction is cooled and the solid which forms is collected by filtration. The solid is dissolved in ethyl acetate-methanol (160 ml, 3 to 1 (v/v)) and filtered through charcoal. The solvent is removed under vacuum and the remaining solid dried under vacuum to yield the product.

Similarly prepared are the 4,5 or 7-(3-carboxypropoxy)-2-sulfamoylbenzo[b]furans.

EXAMPLE 14

6-[2,3-Epoxypropoxy]-2-sulfamoylbenzo[b]furan

Step A: Preparation of 6-allyloxy-2-sulfamoylbenzo[b]furan

The title compound is prepared by alkylation of 6-hydroxy-2-sulfamoylbenzo[b]furan with allyl bromide.

Step B: Preparation of 6-[3(2)-hydroxy-2(3)-bromopropoxy]-2-sulfamoylbenzo[b]furan Treatment of the product from Step A, with N-bromosuccinimide and DMSO provides the title compound.

Step C: Preparation of 6-[2,3-epoxypropoxy]-2-sulfamoylbenzo[b]furan

The subject compound is prepared by treatment of the bromohydrin from Step B with a methanolic KOH solution.

Using the procedures of Example 14, there are also prepared the 4-,5- or 7-(2,3-epoxypropoxy)-2-sulfamoylbenzo[b]furans.

EXAMPLE 15

6-[3-Methoxy-2-hydroxypropoxy]-2-sulfamoylbenzo[b]furan

One drop of concentrated sulfuric acid is added to a solution of 6-[2,3-epoxypropoxy]-2-sulfamoylbenzo[b]furan (7.0 mmol) in methanol (25 ml). After 18 hours, the methanol is removed under vacuum. The residue is dissolved in ethyl acetate (200 ml), washed with water (2×25 ml), brine (2×25 ml) and dried (Na$_2$SO$_4$). The ethyl acetate is removed under vacuum. The white solid remaining is recrystallized from boiling ethyl acetate.

Similarly prepared are the 4-,5- or 7-(3-methoxy-2-hydroxypropoxy)-2-sulfamoylbenzo[b]furans.

EXAMPLE 16

6-(2,3-Dihydroxypropoxy)-2-sulfamoylbenzo[b]furan

Step A: Preparation of N,N-Dimethyl-N'-[[6-(2,2-dimethyl-1,3-dioxolan-3-yl)methoxy]-2-sulfamoylbenzo[b]furan]formamidine The title compound is prepared by treating N,N-dimethyl-N'-[6-hydroxy-2-sulfamoylbenzo[b]furan with 2,2-dimethyl-1,3-dioxolane-4-methanesulfonate in DMSO.

Step B: 6-(2,3-Dihydroxypropoxy)-2-sulfamoylbenzo[b]-furan

Treatment of the product of Step A with warm 6 N hydrochloric acid provides the title compound.

Similarly prepared is the 4-,5- or 7-(2,3-dihydroxypropoxy)-2-sulfamoylbenzo[b]furan.

EXAMPLE 17

5-(2,3-Dihydroxypropoxy)-2-sulfamoylbenzo[b]furan

Step A: N,N-Dimethyl-N'-(5-hydroxy-2-sulfamoylbenzo[b]furan)formamidine

The subject compound is prepared as described in Example 7, Step A.

Step B: Preparation of 5-(2,3-Dihydroxypropoxy)-2-sulfamoylbenzo[b]furan

A suspension of sodium hydride in dry dimethylformamide is treated with N,N-dimethyl-N'-(5-hydroxy-2-sulfamoylbenzo[b]furan)formamidine followed by 2,2-dimethyl-4-hydroxymethyl-1,3-dioxolane methanesulfonate, to provide the title compound.

EXAMPLE 18

5-(Dibenzyl)amino-2-sulfamoylbenzo[b]furan

Step A: Preparation of 5-Dibenzylaminobenzo[b]furan

A stirred solution of 5-aminobenzo[b]furan hydrochloride in dry DMSO is treated with excess benzyl bromide followed by solid NaHCO$_3$ to give the title compound.

Step B: Preparation of 5-(Dibenzyl)amino-2-sulfamoylbenzo[b]furan

The subject compound is prepared by the procedure described in Example 1, Step A, using 5-di(benzyl)aminobenzo[b]furan in place of 5-methoxybenzo[b]furan. The crude product is recrystallized from 1,2-dichloroethane-hexane.

EXAMPLE 19

5-(Dimethyl)amino-2-sulfamoylbenzo[b]furan

Step A: Preparation of
5-(Dimethyl)aminobenzo[b]furan

To a stirred solution of 5-aminobenzo[b]furan in CH$_3$CN is added 37% aqueous formaldehyde followed by sodium cyanoborohydride and glacial acetic acid to give the title compound.

Step B: Preparation of
5-(Dimethyl)amino-2-sulfamoylbenzo[b]furan

The subject compound is prepared by the procedure described in Example 1, Step A, using 5-(dimethyl)aminobenzo[b]furan in place of 5-methoxybenzo[b]furan.

EXAMPLE 20

5-Morpholino-2-sulfamoylbenzo[b]furan

Step A: Preparation of 5-Morpholinobenzo[b]furan

5-Aminobenzo[b]furan and bis-(2-chloroethyl)ether and 40% aqueous NaOH (0.073 mole) are stirred and heated to provide the title compound.

Step B: Preparation of
5-Morpholino-2-sulfamoylbenzo[b]furan

The product of Step A is converted to the title compound by the procedure of Example 1, Step A.

EXAMPLE 21

5-Methyl-2-sulfamoylbenzo[b]furan

5-Methyl-2-sulfamoylbenzo[b]furan is prepared from 5-methylbenzo[b]furan (0.06 mol) using the procedure for the preparation of Example 1, Step A.

EXAMPLE 22

5-Methoxymethyl-2-sulfamoylbenzo[b]furan

Step A: Preparation of 5-Methoxymethylbenzo[b]furan

To a stirred mixture of powdered KOH in dimethylsulfoxide is added 5-hydroxymethylbenzo[b]furan in dimethylsulfoxide. Then methyl iodide is added dropwise at ambient temperature over several minutes to provide the title compound.

Step B: Preparation of
5-Methoxymethyl-2-sulfamoylbenzo[b]furan

5-Methoxymethyl-2-sulfamoylbenzo[b]furan is prepared from 5-methoxymethylbenzo[b]furan (0.059 mol) following the procedure for the preparation described in Example 1, Step A.

EXAMPLE 23

5-Bromomethyl-2-sulfamoylbenzo[b]furan

A suspension of 5-methoxymethyl-2-sulfamoylbenzo[b]furan in dry methylene chloride cooled to −30° C. is treated with boron tribromide to provide the title compound.

EXAMPLE 24

5-Dimethylaminomethyl-2-sulfamoylbenzo[b]furan

An ice cold, stirred solution of 5-bromomethyl-2-sulfamoylbenzo[b]furan in methanol is treated with an excess of anhydrous dimethylamine to give the title compound.

EXAMPLE 25

5-(4-Morpholinylmethyl)-2-sulfamoylbenzo[b]furan

A stirred solution of morpholine and triethylamine in methanol is treated with 5-bromomethyl-2-sulfamoylbenzo[b]furan to give the subject compound.

EXAMPLE 26

5-Acetoxymethyl-2-sulfamoylbenzo[b]furan

A mixture of 5-bromomethyl-2-sulfamoylbenzo[b]furan, anhydrous sodium acetate and glacial acetic acid (15 ml) is treated with a little triethylamine and the mixture is heated to provide the title compound.

EXAMPLE 27

5-Hydroxymethyl-2-sulfamoylbenzo[b]furan

5-Acetoxymethyl-sulfamoylbenzo[b]furan is saponified with KOH to give the title compound.

EXAMPLE 28

5-(2-methoxyethyl)-2-sulfamoylbenzo[b]furan

Step A: Preparation of
5-(2-hydroxyethyl)benzo[b]furan

The subject compound is prepared by a Grignard reaction with the reagant prepared from 5-bromobenzo[b]furan, methyl iodide and magnesium turnings and ethylene oxide.

Step B: Preparation of
5-(2-(methoxyethyl)benzo[b]furan

The title compound is prepared by methylation of the hydroxyethyl intermediate with potassium hydroxide and methyl iodide.

Step C: Preparation of
5-(2-methoxyethyl)-2-sulfamoylbenzo[b]furan

Employing the procedure substantially as described in Example 1, Step A but substituting for the 5-methoxybenzo[b]furan used therein, an equimolar amount of 5-(2-methoxyethyl)benzo[b]furan, there is produced the subject compound.

EXAMPLE 29

5-(2-Benzyloxyethyl)-2-sulfamoylbenzo[b]furan

Step A: Preparation of
5-(2-Benzyloxyethyl)benzo[b]furan

The title compound is prepared by benzylation of 5-(2-hydroxyethyl)benzo[b]furan with benzyl bromide in the presence of sodium hydride.

Step B: Preparation of
5-(2-benzyloxyethyl)-2-sulfamoylbenzo[b]furan

Employing the procedure of Example 1, Step A but using the benzyl ether of Step A of this Example 29 as starting material, the product is produced in approximately the same yield.

EXAMPLE 30

5-(2-Bromoethyl)-2-sulfamoylbenzo[b]furan

This material is prepared by treatment of 5-(2-methoxyethyl)-2-sulfamoylbenzo[b]furan with boron tribromide.

EXAMPLE 31

5-(2-Acetoxyethyl)-2-sulfamoylbenzo[b]furan and
5-2-sulfamoylbenzo[b]furan Treatment of 5-(2-bromoethyl)-2-sulfamoylbenzo[b]furan, with sodium acetate in DMF at 100° C. for about 15 hours provides a mixture which is chromatographed to yield 5-ethenyl-2-sulfamoylbenzo[b]furan and 5-(2-acetoxyethyl)2-sulfamoylbenzo[b]furan.

EXAMPLE 32

5-(2-Hydroxyethyl)-2-sulfamoylbenzo[b]furan

Saponification of 5-(2-acetoxyethyl)-2-sulfamoylbenzo[b]furan in ethanol with 10% aqueous NaOH at reflux provides the title compound.

EXAMPLE 33

6-Hydroxy-2-sulfamoylbenzo[b]furan-6-sodium sulfate

A mixture of 3.00 g of 6-hydroxy-2-sulfamoylbenzo[b]furan and 3.00 g of sulfamic acid in 20 ml of dry pyridine is refluxed gently for 36 hours. At the end of the reaction, the pyridine is distilled from the mixture under vacuum at 50° C. The residue is dissolved in water and made basic by addition of concentrated ammonia. The solvent is evaporated. The product is separated from residual ammonium sulfamate by extraction into ethanol. The ethanol extract is filtered and evaporated to give crude sulfate as the ammonium salt. The salt is dissolved in distilled water and titrated with 1 equivalent of sodium hydroxide. The solvent is evaporated leaving the crude sodium sulfate salt.

Treating the ammonium salt produced in Example 33 with potassium hydroxide, tetramethylammonium hydroxide, pyridine, imidazole, pralidoxime hydroxide or thiamine in place of the sodium hydroxide used in Example 33 there are prepared the corresponding salts.

EXAMPLE 34

6-Hydroxy-2-sulfamoylbenzo[b]furan-6-disodium phosphate

A solution of 2.5 g of 6-hydroxy-2-sulfamoylbenzo[b]furan in 10 ml of pyridine is added over a 1 minute period to a well-stirred solution of 1 equivalent of phosphorous oxychloride in pyridine (10 ml) at 0° C. After 15 to 30 minutes the reaction mixture is poured into ice-water and the resulting solution is stirred for 15 minutes. The solvents are evaporated under high vacuum on a rotary evaporator. The product is resuspended in water and the pH of the solution is adjusted to 7.8±0.6. The solvents are removed and the solid dried under high vacuum.

Other salts of the phosphate group are obtained by using the appropriate hydroxide in place of sodium hydroxide in the procedure above, such as potassium hydroxide, tetramethylammonium hydroxide, pyridine, imidazole, pralidoxime hydroxide and thiamine.

Mixed esters of the type:

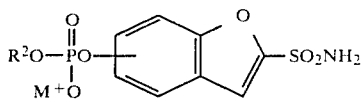

wherein $R^2$ is $C_{1-3}$alkyl or phenyl-$C_{1-3}$alkyl are prepared by reacting a hydroxy-2-sulfamoylbenzo[b]furan with an appropriate alkyldichlorophosphate; e.g. ethyldichlorophosphate, or benzyldichlorophosphate.

For use in treatment of conditions relieved by the inhibition of carbonic anhydrase, the active compound can be administered either systemically, or, in the treatment of the eye, topically. The dose administered can be from as little as 0.1 to 25 mg or more per day, singly, or preferably on a 2 to 4 dose per day regimen although a single dose per day is satisfactory.

When administered for the treatment of elevated intraocular pressure or glaucoma, the active compound is most desirably administered topically to the eye, although systemic treatment is, as indicated, also possible.

When given systemically, the drug can be given by any route, although the oral route is preferred. In oral administration the drug can be employed in any of the usual dosage forms such as tablets or capsules, either in a contemporaneous delivery or sustained release form. Any number of the usual excipients or tableting aids can likewise be included.

When given by the topical route, the active drug or an ophthalmologically acceptable salt thereof such as the sodium or potassium salt is formulated into an ophthalmic preparation. In such formulations, from 0.1% to 15% by weight can be employed. The objective is to administer a dose of from 0.1 to 10 mg per eye per day to the patient, with treatment continuing so long as the condition persists.

Thus, in an ophthalmic solution, insert, ointment or suspension for topical delivery, or a tablet, intramuscular, or intravenous composition for systemic delivery, the active medicament or an equivalent amount of a salt thereof is employed, the remainder being carrier, excipients, preservatives and the like as are customarily used in such compositions.

The active drugs of this invention are most suitably administered in the form of ophthalmic pharmaceutical compositions adapted for topical administration to the eye such as a suspension, ointment, or as a solid insert. Formulations of these compounds may contain from 0.01 to 15% and especially 0.5% to 2% of medicament. Higher dosages as, for example, about 10%, or lower dosages can be employed provided the dose is effective in reducing or controlling elevated intraocular pressure. As a unit dosage from between 0.001 to 10.0 mg, preferably 0.005 to 2.0 mg, and especially 0.1 to 1.0 mg of the compound is generally applied to the human eye, generally on a daily basis in single or divided doses so long as the condition being treated exists.

These hereinbefore described dosage values are believed accurate for human patients and are based on the known and presently understood pharmacology of the compounds, and the action of other similar entities in the human eye. They reflect the best mode known. As with all medications, dosage requirements are variable and must be individualized on the basis of the disease and the response of the patient.

The pharmaceutical preparation which contains the active compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

The pharmaceutical preparation may also be in the form of a solid insert such as one which after dispensing the drug remains essentially intact, or a bio-erodible insert that either is soluble in lacrimal fluids, or otherwise disintegrates.

The following examples of ophthalmic formulations are given by way of illustration.

EXAMPLE 35

| | | |
|---|---|---|
| 5-Hydroxy-2-sulfamoyl-benzo[b]furan (I) | 1 mg. | 15 mg. |
| Monobasic sodium phosphate .2H$_2$O | 9.38 mg. | 6.10 mg. |
| Dibasic sodium phosphate .12H$_2$O | 28.48 mg. | 16.80 mg. |
| Benzalkonium chloride | 0.10 mg. | 0.10 mg. |
| Water for injection q.s. ad. | 1.0 ml. | 1.0 ml. |

Compound I, phosphate buffer salts, and benzalkonium chloride are added to and dissolved in water. The pH of the composition is adjusted to 6.8 and diluted to volume. The composition is rendered sterile by ionizing radiation.

EXAMPLE 36

| | |
|---|---|
| 6-(2-Sulfamoylbenzo[b]furyl) 2-methylpropionate (II) | 5 mg. |
| petrolatum q.s. ad. | 1 gram |

Compound II and the petrolatum are aseptically combined.

EXAMPLE 37

| | |
|---|---|
| 5-(2-Sulfamoylbenzo[b]furyl) acetate | 1 mg. |
| Hydroxypropylcellulose q.s. | 12 mg. |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

EXAMPLE 38

| | |
|---|---|
| 6-(2-Sulfamoylbenzo[b]furyl) acetate | 1 mg. |
| Hydroxypropyl cellulose q.s. ad. | 12 mg. |

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R. H. cabinet until it is pliable. Appropriately sized inserts are cut from the film.

EXAMPLE 39

| | |
|---|---|
| 5-Hydroxy-2-sulfamoylbenzo-[b]furan | 1 mg. |
| Hydroxypropylmethyl cellulose q.s. ad. | 12 mg. |

Ophthalmic inserts are manufactured from a solvent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R. H. cabinet until it is pliable. Appropriately sized inserts are then cut from the film.

EXAMPLE 40

| | |
|---|---|
| 6-(2-Sulfamoylbenzo[b]furyl) acetate | 1 mg. |
| Hydroxypropylmethyl cellulose q.s. ad. | 12 mg. |

Ophthalmic inserts are manufactured from compression molded films which are prepared on a Carver Press by subjecting the powdered mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R. H. at 30° C.) for two to four days. After removal from the humidity cabinet, the vials are stoppered and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and to insure against recontamination, the sterilization is preferably conducted after packaging. The best mode of sterilizing is to employ ionizing radiation including radiation emanating from Cobalt 60 or high energy electron beams.

What is claimed is:

1. A compound of structural formula:

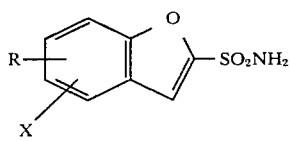

or an ophthalmologically or pharmaceutically acceptable salt thereof, wherein:
X is halogen, chloro, bromo or fluoro, $C_{1-3}$alkyl, hydroxy or $C_{1-3}$alkoxy; and
R is
(1) hydroxy,
(2) $R_a^1$ wherein $R_a^1$ is
  (a) $C_{1-18}$alkyl either straight or branched chain and substituted with one or more of
    (i) $C_{3-6}$cycloalkyl,
    (ii) halo,
    (iii) aryl, wherein the aryl group is phenyl, naphthyl, pyridinyl, furanyl, pyrazinyl, imidazolyl or thienyl and wherein the aryl group can be substituted with one or more of $C_{1-10}$alkyl, halo, $C_{1-4}$alkoxy or $C_{2-5}$alkanoyl,
    (iv) hydroxy,
    (v) $C_{1-3}$alkoxy,
    (vi) aryl-$C_{1-3}$alkoxy, wherein aryl is as previously defined,
    (vii) amino,
    (viii) ($C_{1-3}$alkyl)amino,
    (ix) di($C_{1-3}$alkyl)amino
    (x)

wherein $R^2$ is
  (1) HO—,
  (2) $M^+O^-$, wherein $M^+$ is a pharmaceutically acceptable cation,
  (3) $C_{1-10}$alkoxy,
  (4) $R^3R^4N$— wherein $R^3$ and $R^4$ are independently hydrogen, $C_{1-15}$alkyl, or taken together form a 3–7 membered heterocycle, selected from piperidino and pyrrolidino, with the nitrogen to which they are attached,
  (b) $C_{3-6}$cycloalkyl,
  (c) $C_{1-18}$alkyl-$C_{3-6}$cycloalkyl,
  (d) aryl as previously defined,
  (e) $C_{2-6}$alkenyl,
  (f) aryl-$C_{2-6}$alkenyl, wherein aryl is as previously defined, or
  (g) $C_{2-6}$alkynyl;
(3) $R_a^1$—O—,
(4)

wherein $R^1$ is $R_a^1$ or $C_{1-18}$alkyl,
(5)

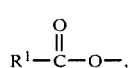

(6)

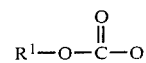

(7)

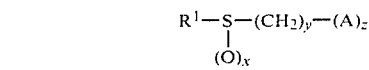

wherein x is 0–2; y is 0–3; z is 0 or 1; and A is a heteroatom selected from S, O and N,
(8)

wherein $R^5$ and $R^6$ are independently:
(a) hydrogen,
(b) $C_{1-18}$alkyl, either straight or branched chain,
(c) $C_{3-6}$cycloalkyl,
(d) $C_{3-6}$cycloalkyl-$C_{1-3}$alkyl,
(e) aryl-$C_{1-3}$alkyl wherein the aryl group is as previously defined and is either unsubstituted or substituted with one or more of chloro, bromo, fluoro, $C_{1-3}$alkyl or $C_{1-3}$alkoxy,
(f)

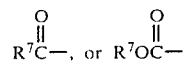

wherein $R^7$ is
  (i) $C_{1-18}$alkyl, either straight or branched chain,
  (ii) aryl as previously defined, either unsubstituted or substituted with one or more of chloro, bromo, fluoro, $C_{1-3}$alkyl, or $C_{1-3}$alkoxy,
  (iii) aryl-$C_{1-3}$alkyl wherein the aryl group is as previously defined and is either unsubstituted or substituted with one or more of chloro, bromo, fluoro, $C_{1-3}$alkyl or $C_{1-3}$alkoxy,
  (iv) amino-$C_{1-18}$alkyl either straight or branched chain; or
(g) $R^5$ and $R^6$ if lower alkyl, are joined together directly or through a heteroatom selected from O or N to form a 5 or 6 membered heterocycle with the nitrogen to which they are attached selected from pyrrolidine, piperidine, morpholine and piperazine;
(9)

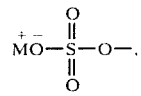

wherein $M^+$ is an ophthalmologically acceptable cation selected from sodium, potassium, ammonium, tetra($C_{1-4}$alkyl)ammonium, pyridinium, imidazolium, pralidoxime, and thiamine
(10)

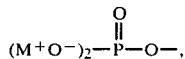

wherein M+ is as previously defined;

(11)

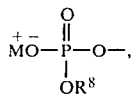

wherein $R^8$ is $C_{1-3}$alkyl or phenyl-$C_{1-3}$alkyl; or (12)

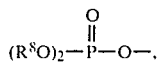

wherein $R^8$ is as previously defined, and the two may be the same or different.

2. The compound of claim 1, wherein R is in the 5 or 6 position.

3. The compound of claim 2, wherein X is hydrogen, R is HO—,

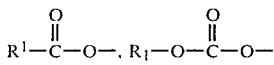

or $R^5R^6N$—.

4. The compound of claim 3, wherein $R^1$ is $C_{1-18}$ alkyl.

5. The compound of claim 3, wherein $R^1$ is $C_{1-4}$ alkyl.

6. The compound of claim 3, which is:
5 (or 6)-hydroxy-2-sulfamoylbenzo[b]furan;
5 (or 6)-(2-sulfamoylbenzo[b]furyl) acetate;
5 (or 6)-(2-sulfamoylbenzo[b]furyl) 2,2-dimethylpropionate;
5 (or 6)-(2-sulfamoylbenzo[b]furyl) 2-methylpropionate; or
5 (or 6)-(2-sulfamoylbenzo[b]furyl) 3-ethoxycarbonylpropionate.

7. An ophthalmic composition for the topical treatment of glaucoma and elevated intraocular pressure comprising an ophthalmologically acceptable carrier and an effective intraocular pressure lowering amount of a compound with structural formula:

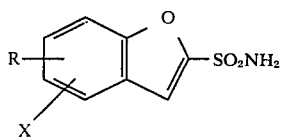

or an ophthalmologically acceptable salt thereof, wherein R and X are as defined in claim 1.

8. The composition of claim 7, wherein R is in the 5 or 6 position.

9. The composition of claim 8, wherein X is hydrogen, R is HO—,

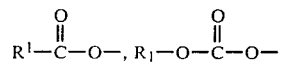

or $R^5R^6N$—.

10. The composition of claim 9, wherein $R^1$ is $C_{1-18}$ alkyl.

11. The composition of claim 9, wherein $R^1$ is $C_{1-4}$ alkyl.

12. The composition of claim 9, wherein the compound is:
5 (or 6)-hydroxy-2-sulfamoylbenzo[b]furan;
5 (or 6)-(2-sulfamoylbenzo[b]furyl) acetate;
5 (or 6)-(2-sulfamoylbenzo[b]furyl) 2,2-dimethylpropionate;
5 (or 6)-(2-sulfamoylbenzo[b]furyl) 2-methylpropionate; or
5 (or 6)-(2-sulfamoylbenzo[b]furyl) 3-ethoxycarbonylpropionate.

13. A method of treating glaucoma and elevated intraocular pressure which comprises topical ocular application to a patient in need of such treatment of an effective intraocular pressure lowering amount of a compound with structural formula:

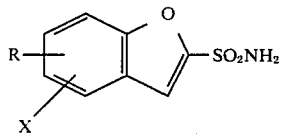

or an ophthalmologically acceptable salt thereof, wherein R and X are as defined in claim 1.

14. The method of claim 13, wherein R is in the 5 or 6 position.

15. The method of claim 14, wherein X is hydrogen, R is HO—,

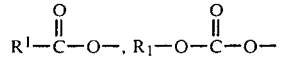

or $R^5R^6N$—.

16. The method of claim 15, wherein $R^1$ is $C_{1-18}$alkyl.

17. The method of claim 15, wherein $R^1$ is $C_{1-4}$alkyl.

18. The method of claim 15, wherein the compound is:
5 (or 6)-hydroxy-2-sulfamoylbenzo[b]furan;
5 (or 6)-(2-sulfamoylbenzo[b]furyl) acetate;
5 (or 6)-(2-sulfamoylbenzo[b]furyl) 2,2-dimethylpropionate;
5 (or 6)-(2-sulfamoylbenzo[b]furyl) 2-methylpropionate; or
5 (or 6)-(2-sulfamoylbenzo[b]furyl) 3-ethoxycarbonylpropionate.

* * * * *